(12) United States Patent
Chua et al.

(10) Patent No.: US 6,344,601 B1
(45) Date of Patent: Feb. 5, 2002

(54) ALTERATION OF PLANT MORPHOLOGY BY CONTROL OF PROFILIN EXPRESSION

(75) Inventors: Nam-Hai Chua, Scarsdale, NY (US); Srinivasan Ramachandran, Singapore (SG); Hans Erik Molager Christensen, Hedehusene (DK)

(73) Assignee: Institute of Molecular Agrobiology (SG)

( * ) Notice: Subject to any disclaimer, the term of this patent is extended or adjusted under 35 U.S.C. 154(b) by 0 days.

(21) Appl. No.: 09/061,897

(22) Filed: Apr. 17, 1998

(30) Foreign Application Priority Data

Apr. 17, 1997 (SG) .......................... 9701243-9

(51) Int. Cl.[7] ........................ C12N 15/82; C12N 15/90; C12N 5/09; A01H 5/00
(52) U.S. Cl. ..................... 800/290; 435/69.1; 435/419; 435/468; 800/298
(58) Field of Search ................ 435/69.1, 419, 435/410, 430; 536/23.6; 800/278, 290, 295, 298

(56) References Cited

FOREIGN PATENT DOCUMENTS

| WO | WO 96/37614 | * 11/1996 | ........... C12N/15/29 |
|----|-------------|-----------|------------------------|
| WO | 9942600 | 8/1999 | ........... C12N/15/82 |

OTHER PUBLICATIONS

Vidali et al, Plant Physiol., vol. 108, pp. 115–123 1995.*
Ramachandran et al., "Roles of actin–binding proteins in plant development," AGRICOLA database entry, Accession No. 1999:59947.
Christensen et al., "Arabidopsis profilins are functionally similar to yeast profilins: identifcation of a vascular bundle–specific profilin and a pollen–specific profilin," The Plant Journal 10(2):269–279 (1996).
Staiger et al., "Microinjected profilin affects cytoplasmic streaming in plant cells by rapidly depolymerizing actin microfilaments," Current Biology 4(3):215–219 (1994).
Huang et al., "The Arabidopsis Profilin Gene Family," Plant Physiology 111(1):115–126 (1996).

* cited by examiner

*Primary Examiner*—Gary Benzion
*Assistant Examiner*—Ashwin Mehta
(74) *Attorney, Agent, or Firm*—Rothwell, Figg, Ernst & Manbeck

(57) ABSTRACT

Plant growth habit is altered by causing either under-expression or over-expression of profilin in a plant cell. Under-expression of profilin can be achieved by transforming a plant or plant cell with a gene expressing an antisense mRNA complementary to the mRNA transcribed by the coding sequence of a profilin gene and expressing the gene in the plant or plant cell such that the antisense mRNA inhibits the production of the profilin in the plant or plant cell. Under-expression of profilins in plants can lead to such alterations in growth habit as a dwarf phenotype, a reduced root and root hair system, and delay in the onset of flowering. Over-expression of profilin can be achieved by transforming a plant or plant cell with a gene capable of expressing a profilin in the plant or plant cell and causing the transformed gene to be expressed in the plant or plant cell. Over-expression of profilin in a plant can lead to such alterations in growth habit as a tall phenotype, an expansion of the root and root hair system, expansion of leaf surface area and accelerating the onset of flowering.

9 Claims, No Drawings

ALTERATION OF PLANT MORPHOLOGY BY CONTROL OF PROFILIN EXPRESSION

TECHNICAL FIELD

The present invention relates to the in vivo effects of profilin in plant cells. In particular, it has been found that manipulation of the level of expression of profilins in plants can lead to useful alterations in plant phenotype.

BACKGROUND OF THE INVENTION

Actin is the major cytoskeletal protein of most eukaryotic cells and actin filaments are often the primary determinants of cell shape and movement. The polymerization and depolymerization of actin filaments inside the non muscle cells are highly regulated, both spatially and temporally, to give the cell the ability to rearrange its cytoskeleton drastically within minutes in response to external stimuli or at a point of the cell cycle. In addition to the roles in cell shape and movements, the actin cytoskeleton in plants has been shown to play a role in cytoplasmic streaming, cytokinesis, cell expansion and plant development (Williamson, 1993; Meagher and Williamson, 1994). To achieve these dynamic rearrangements the cell relies on a variety of actin-binding proteins.

Profilin is an ubiquitous actin-monomer binding protein whose homologs are present in organisms ranging from fungi and amoebae through higher plants and mammals. They are low molecular mass (12–15 Kd), actin-binding proteins involved in the regulation of actin dynamics. Apart from actin-binding, profilins also bind to phosphatidylinositol 4,5-bisphosphate (PIP2)(Sohn et al., 1995), poly-L-proline (Bjorkegren et al., 1993) and a proline rich VASP (Reinhard et al., 1995; Haffner et al., 1995). Evidence suggests that profilin is a multi-functional protein (Haarer et al., 1990) which exerts both positive and negative effects on the actin polymerization (Theriot and Mitchison, 1993) and is involved in signal transduction pathways (Sohn and Goldschmidt-Clermont, 1994).

In vitro studies showed that profilin can lower the critical concentration for actin polymerization, stimulate polymerization and promote nucleotide exchange on actin monomers (for reviews see Theriot and Mitchison, 1993; Sohn and Goldschmidt-Clermont, 1994 and Sun et al., 1995). In vivo studies on profilin functions also yielded mixed results. Profilin mutations affected multiple actin-dependent processes in Drososphila (Verheyen and Cooley, 1994), blocked yeast cell budding (Haarer, 1990) and cytokinesis, as they cannot assemble the contractile rings, in *Schizosaccharomyces pombe* (Balasubramanian et al., 1994). Recent studies on *Dictyostelium discoideum* showed 60 to 70% increase in F-actin content at the rim below the plasma membrane when both profilins are deleted (Haugwitz et al., 1994). Microinjection of profilin into animal (Cao et al., 1992) or plant (Staiger et al., 1994) cells depolymerized actin. Profilin overexpression in stably transformed cells increased polymerization of actin at the cell periphery by prolonging cortical actin filament half-life (Finkel et al., 1994).

In addition to the above functions, profilin has been shown to be involved in at least two signal transduction pathways. They are the growth factor mediated receptor tyrosine kinase pathway and the Ras/G protein signaling pathway (for a review see Sohn and Goldschmidt-Clermont, 1994). Profilin has shown to bind PIP2 with high affinity and inhibits unphosphorylated phospholipase C (Goldschmidt-Clermont et al., 1990 and Drobak et al., 1994). This inhibition is overcome by growth factor mediated phosphorylation of phospholipase C (Goldschmidt-Clermont et al. 1991). The cyclase associated protein (CAP)/Srv2p is a component of the Ras/G protein signaling pathway and an yeast mutant of CAP was rescued by profilin, which suggested a possible role for profilin in this pathway (Vojtek et al., 1991). Profilin can bind to actin or PIP2 simultaneously with poly-L-proline proteins and proline rich sequences found in many proteins (Reinhard et al., 1995). This interaction with proteins that have proline rich sequences suggested a role for profilin in mediating membrane-cytoskeletal communications by physically attaching signaling proteins to plasma membrane and/or cytoskeleton.

In plants profilin has been identified and characterized in several species including maize pollen and tobacco (Staiger et al., 1993 and Mittermann et al., 1995), leaves and root nodules of *Phaseolus vulgaris* (Vidali et al., 1995) and *Arabidopsis thaliana* (Huang et al., 1996 and Christensen et al., 1996). Plant profilins have been shown to bind plant and animal actin In vitro (Valenta et al., 1993; Giehl et al., 1994 and Ruhlandt et al., 1995). Recently Perelroizen et al. (1996) reported that Arabidopsis profilin, like other profilins, can bind G-actin and promote assembly of actin filaments at the barbed end in vitro. In contrast to other profilins, Arabidopsis profilins do not accelerate the nucleotide exchange on actin. Despite these advances in plant profilin studies, there have been no reports so far on the in vivo functional analysis of profilins in plants.

SUMMARY OF THE INVENTION

We have found that over-production of profilin in plants or plant cells, preferably achieved by transformation of a plant or plant cell with a chimeric profilin gene that is highly expressed in plants, can cause increased cell elongation in growing plants. One of the results of this effect is a plant with a "tall" phenotype compared to the non-transgenic control plant. Another result is elongation of the root and root hair system of the plant.

We have also found that under-production of profilin, preferably achieved by reducing expression of native profilin in a plant (such as by the use of antisense RNA), can cause decreased cell elongation. One of the results of this is a "dwarf" phenotype.

It is also possible to direct over-expression or under-expression to specific tissues of the plant, such as root tissues. This results in a selective effect on the growth of that tissue. In one embodiment, a profilin coding sequence is linked to a root-specific promoter, resulting in elongation of roots, and particularly root-hairs. This increase in root surface area increases the plant's capacity to absorb water and nutrients, making it more drought-resistant, for instance, or less dependent on chemical fertilizers.

Control of the level of profilin production can also effect control of plant flowering time. It has been found that over-production of profilin by a plant leads to a delay in flowering time, while under-production of profilin promotes early flowering.

Such control of plant stature and flowering time has many applications in the creation of agricultural and horticultural varieties of plants.

DETAILED DESCRIPTION

The present invention takes advantage of the in vivo functions of plant profilins to effect changes in plant morphology, growth and flowering. It has been found that altering the level of expression of profilin in a plant cell leads to alterations in cell morphology and in cell elongation. At an organismic level, these changes can effect the growth habit of the plant, as well as effect the onset of flowering.

In an embodiment of the invention, a study was made of the in vivo functions of the *Arabidopsis thaliana* profilin-1 gene. Transgenic plants over- and under-expressing profilin-1 were generated by transforming wild type Arabidopsis plants with sense or antisense constructs under the control of a 35S promoter. Etiolated transgenic seedlings under-expressing profilin-1 exhibited overall stunted growth, short hypocotyl and at low temperature they were only 15 to 20% long when compared with the wild type plants. Light grown plants also showed the reduced growth and these plants flowered early. Light and electron microscopic observations of the hypocotyl surface and sections of the etiolated seedlings revealed that the surface of these seedlings were ruffled with some electron dense particle accumulation and enlarged epidermal, cortical and endodermal cells. The epidermal and cortical cells also showed defective vesicular transport with fibrous and electron dense particles and vesicles accumulating in the cytoplasm and close to the plasma membrane. On the other hand, the etiolated transgenic seedlings over-expressing profilin-1 were slightly bigger than the wild type in light and at normal and low temperature. Microscopic analysis of these seedlings showed no obvious changes compared to the wild type, except that the epidermal, cortical and endodermal cells were bigger. Light grown plants showed a flowering time delayed by at least by a week. Actin staining on the etiolated seedlings over or under expressing profilin-1 showed normal actin staining pattern with networks in the cotyledon cells and petiole cells. Transgenic seedlings harboring the profilin-1 promoter-Gus construct showed the Gus expression as a ring at the elongating zone of the root meristems and the root hairs. These changes were inheritable, even to the fourth generation.

It is frequently desirable in horticulture and agriculture to have plant varieties that have a taller or shorter growth habit in respect to the "wild type" of the species or variety. For instance, in rice a "tall" variety is better able to survive flooding conditions by growing higher above the water level. Conversely, a "dwarf" variety of beans grows as a bush instead of a vine, taking up less space, requiring little or no physical support during growth and facilitating harvest. Tall and dwarf ornamental varieties are also much sought after. Other situations where at taller or shorter plant phenotype would be advantageous are readily apparent to persons skilled in the art. Some further examples of applications for this invention are the creation of miniature vegetables and fruit trees; leafy vegetables, tomatoes, peppers etc., and reduction in the flowering time of ornaments (such as orchids).

There are instances where enlargement of a particular part of the plant would be desirable. A particularly good example of this is the advantage conferred to a plant by an expanded root and root hair system. Roots serve not only to anchor the plant in the soil, but also as the means by which the plant absorbs nutrients and water from the soil. This absorption is achieved by the root hairs, fine cellular elongations at the tips of roots. A well-developed root hair system is crucial to plant survival. A plant that has an expanded root system, and in particular an expanded system of root hairs, is better able to absorb nutrients and water from the soil. The enhanced ability to take up water is particularly advantageous for plants grown in drought-prone or water-poor environments, and provides increased tolerance to water stress.

For many crops where the harvest consists of the flower, fruit or seed, yield is effected by the size of the plant at the time of flowering. The larger the plant, the greater is its capacity to flower prolifically and bear a large crop. Thus, delaying the onset of flowering can frequently lead to higher yields by allowing the plant to grow larger before diverting its metabolic energy to flower, fruit and seed production. Conversely, a rapid onset of flowering can be advantageous in an environment where the growing season is relatively short. Early flowering permits a crop to mature for harvest before climatic conditions become unfavorable to plant growth.

According to the present invention, it has been found that over-production of profilin in a plant cell leads to increased cell elongation. At the gross level, the overall effect on the plant is a "tall" growth habit and general enlargement of plant parts, including leaves and the root and root hair systems. Over-production of profilin can be achieved in several ways. A preferred way of achieving over-production is to transform a plant or plant cell with a gene construct that expresses high levels of profilin in vivo. High levels of gene expression can be obtained, for example, by using a naturally-occurring highly-expressed profilin coding sequence. Some examples of highly-expressed profilins are Profilin 1 and 2. Another method of achieving high levels of expression is to link a profilin coding sequence to a highly active plant promoter, preferably along with one or more promoter enhancer sequences. Several highly active plant promoters are known in the art, such as the cauliflower mosaic virus (CaMV) 35S promoter, the opine synthase promoters (mannopine synthase promoter, nopaline synthase promoter, etc.) Selective expression of profilin in particular plant tissues can be achieved by the use of tissue-specific promoters known in the art, such as perfect palindronic sequence tetramer fused 10–90 S35 promoter (Salinas et al., 1992). Selection of appropriate promoters and enhancers for use in the invention is within the ordinary skill in the art. Preferably, a combination of the above approaches to enhancing expression is used, e.g. a naturally highly-expressed sequence is linked to an active promoter with one or more enhancer sequences.

Once the gene is obtained, it can be transformed into the host by any conventional means. Examples of plant transformation techniques currently known in the art are the calcium phosphate method, electroporation, microparticle bombardment, *Agrobacterium tumefaciens* infection, PEG transformation, vacuum infiltration and in planta approach. The selection and use of an appropriate transformation method is well within the skill of the person of ordinary skill in the art. Preferably, stable transformation is achieved, meaning that the introduced sequences are stably integrated into the plant genome (be it into the nuclear, chloroplast or mitochondrial chromosomes, or into two or all of these). A transgenic plant can be grown from a transformed plant cell or cell culture by any of several standard tissue culture and regeneration techniques within the skill of the art. If a growing plant or plant part is transformed, a whole transformed plant can be obtained by methods such as vegetative propagation of the plant part, again by methods within the ordinary skill in the art.

The present invention has also shown that under-production of profilin in a plant cell leads to a decrease in cell elongation and plant part size. The overall effect of this is a plant with a "dwarf" growth habit. Like profilin over-production, under-expression of profilins can be achieved in several ways. Preferably, a gene encoding an antisense RNA complementary to the native plant profilin gene is introduced into the plant. A simple way of doing this is to link a plant promoter to a copy of the plant profilin coding sequence oriented in the antisense direction. The "backwards" coding sequence will be transcribed into an mRNA complementary to the native plant profilin mRNA transcribed from the native coding sequence. The antisense mRNA prevents expression of profilin, most likely by co-suppression of the profilin gene. The techniques of gene construction, transformation and regeneration described above can be equally applied in this embodiment of the invention.

MATERIALS AND METHODS

Plant Materials and Growth Conditions

*Arabidopsis thaliana* C24 ecotype was used. Seeds were surface sterilized with 10% bleach and washed three times with sterile deionized water. After the final wash, 0.2% agarose was added to the seeds and plated on MS media with 3% Sucrose. Plates were incubated at 4° C. for two days and then treated with white light for two hours to induce germination. For growth in the dark plates were wrapped with three layers of aluminum foil and kept vertically in a tissue culture room at 22°. For the cold treatment, the wrapped plants were kept vertically in a refrigerator for 4 weeks. For light growth, plates were exposed to 16 hr. light/8 hr. Dark at 22°. After three weeks the seedlings were potted in soil and grown in a growth chamber with a photoperiod of 16 hours and humidity of 75%.

Vector Constructions and Plant Transformations

The coding region of profilin-1cDNA (Christensen et al., 1996) was cloned downstream of a 35S promoter contained in a binary plasmid pVIP40 in sense and in antisense orientations. For the profilin-1 promoter-Gus fusion constructs 1.0 Kb of the profilin-1 promoter was cloned in pVIP 40 Vector. *Arabidopsis thaliana* C24 roots were used as the plant material for transformation. T3 transgenic lines were generated and used to obtain homozygous T4 seeds. Two independent lines for profilin-1 over-expression and three lines for under-expression were used.

Northern Analysis

Total RNA was extracted using a Qigen RNA isolation Kit, from 10-day old dark grown or light grown seedlings of wild type (WT) and transgenic plants. 10 $\mu$g of total RNA was used for the WT and the PFN-0 (profilin-over expressing lines) lines and 30 $\mu$g for the PFN-U (profilin-under expressing lines) lines were loaded on 1.2% agarose gels and electrophoresed. RNA samples were blotted on to a nylon membrane which was used for hybridizations. Radiolabelled antisense strand of profilin-1 was transcribed from the profilin-1 cDNA cloned in pBlueScript and used as a probe for the hybridizations. Arabidopsis actin-7 cDNA and ADF-1 cDNA were used to make radiolabelled probes for the blots to analyze actin and ADF expression levels in profilin transgenic plants. 18S rRNA was used as an internal control to normalize the loading amounts of RNA samples.

Generation of Antibody, SDS-PAGE and Western Blotting

Profilin-1 and Profilin-3 proteins were expressed as a recombinant protein in *E. Coli* (Christensen et al., 1996) and was used to immunize the rabbits to obtain polyclonal antibodies. The antisera was affinity purified on a Protein A Sepharose CL-4B (Pharmacia) column and was used for the analysis. Ten day old (light or dark grown) seedlings grown at 22° C. or 4 weeks old etiolated seedlings grown at 4° C. were used as the plant material for protein extraction for western blots. The plant materials were extracted on ice with 50 mM Tris-Cl (pH 8.0), 0.5 mM Calcium Chloride, 0.5% NP40, 0.5 mM βME and Aprotinin and Leupeptin (1 $\mu$g/ml). The contents were centrifuged for 10 minutes at 4° C. and the supernatant was collected. The protein concentrations were determined by Bradford's method and 20 $\mu$g was loaded on 15% polyacrylamide gels (Laemmli, 1970).

Proteins were then transferred to the nitrocellulose membrane and processed further. Membranes were blocked with 3% non-fat milk in PBS buffer containing 0.05% Tween-20 for an hour and washed several times followed by overnight incubation with affinity purified anti-profilin-1. The membranes were then washed with PBS and treated with alkaline phosphatase conjugated anti-rabit IgG (Promega) and incubated for an hour. After several washes the bands were developed using the substrate cocktail. For actin protein and ADF protein level detection we used the antibodies raised against actin. Actin-7 fusion protein was expressed in *E. coli* and the purified recombinant protein was used to raise antibodies in rabbits and ADF. ADF-1 fusion protein was expressed in *E. coli* and the purified recombinant protein was used to raise antibodies in rabbits.

Cell Length and Diameter Measurements

Longitudinal and cross sections of wild type and transgenic,seedlings grown for 10 days in the dark were photographed under the light microscope. The length and diameter of the epidermal and cortex cells were measured on the enlarged photograph. More than 50 cells of each plant were used for the measurements.

Flowering Time (FT) and Leaf Number (LN)

FT of wild type and transgenic plants were scored as the number of days from the time when the plates were placed in the tissue culture room to the time of opening of the first flower. Leaf number was scored as the number of leaves on the rosette (excluding cotyledon) and the main flowering stalk at the time of opening of the first flower. Three weeks after germination about 15 randomly selected plants from the wild type and each of the two independent lines of over- and three of the under-expressing transgenic plants were transferred in soil.

Microscopy

Ten day old etiolated seedings in fixation buffer were kept on ice, subjected to 30 sec microwave oven treatment, followed by fixation in 0.1M cacodylate buffer (pH 7.4) containing 4% paraformaldehyde, 5% glutaraldehyde and 0.1M $CaCl_2$ for three hours. The seedlings were then washed with 0.1M cacodylate buffer for 1.5 hours and post-fixed for three hours with 2% osmium tetroxide. Dehydration with an ethanol series and propylene oxide was carried out and embedded in Spurr resin (Electron Microscopy Sciences, Fort Washington, Pa.). Semi-thin sections were stained with toluidine blue for light microscopy analysis.

For scanning electron microscopic observation, the specimens were fixed in PBS buffer (pH 7.3) containing 2.5% glutaraldehyde and 2% paraformaldehyde at 4° C. for 2.5 hours, followed by dehydration through a gradient concentration of ethanol. Samples were then dried in liquid carbon dioxide on Samdri-780u (Tousimis Research Corporation, Rockville, Md.), mounted on stubs, sputter coated with gold, and examined with a scanning electron microscope (model JSM-T220A; JEOL Ltd., Tokyo, Japan) at an accelerating voltage of 20 Kv.

β-Glucuronidase (GUS) Assay

Gus assay was performed histochemically with 5 bromo-4-chloro-3-indoyl glucuronide (X-Gluc, Jefferson, 1987) as the substrate using a protocol adapted from Toriyama et al. (1991). The entire seedlings were submerged in the GUS-stain solution (2 mM X-Gluc, 0.1M sodium phosphate buffer, pH 7.0, 0.5% Triton X-100, 2 mM $K_3[Fe(CN)6]$, 2 mM $K_4[Fe(CN)_6]$, and 0.2% $NaN_3$) and vacuum infiltrated for about 10 minutes and then incubated at 37° C. overnight.

The reaction was stopped and then the plant material cleared by rinsing and incubation with 70% ethanol overnight at 37° C.

Actin Staining

Wild type and transgenic etiolated seedlings (10 days old) were placed in an Eppendorf tube containing a slurry of EZE-LAP, lapping compound #700 WF (Scour Pads, Australia), in phosphate buffer (pH 7.2) and vortexed for 1 minute. After washing three times with phosphate buffer, the top portion of seedlings including cotyledons, petioles, hook and a portion of hypocotyl were cut off and incubated in fluorescein-phalloidin (Molecular Probes, U.S.A.) in phosphate buffer for two hours. The specimens were mounted on a glass slide with the same stain solution and cortical actin patterns of epidermal cells were visualized using a confocal microscope (MRC 600 or MRC 1024, BioRad). In case of fixation, the seedlings were incubated in 4% paraformaldehyde in phosphate buffer for 45 minutes and then washed two times with phosphate buffer followed by EZE-LAP treatment as described above.

EXAMPLE 1

Generation and Analysis of PFN-O and PFN-U Plants

Our lab previously (Christensen et al., 1996) reported the identification and molecular analysis of four profilin genes including profilin-1 in *Arabidopsis thaliana*. In order to identify the in vivo functions of profilin-1 transgenic Arabidopsis plants over-expressing (PFN-O) and under-expressing (PFN-U) this protein were generated as described above in the materials and methods. PFN-U plants showed dwarf phenotype and flowered earlier than the control, whereas the PFN-O plants showed no severe phenotype or slightly taller phenotype than the control. To confirm that these changes in the transgenic plants are in fact due to over and under-expression of profilins, northern and western blot analysis were performed as described above in the materials and methods. Five lines of PFN-U plants showed 25% to 50% reduction in profilin RNA and protein levels than the control and out of these three lines were selected for further studies. On the other hand, only two lines of PFN-O plants showed at least 20 times more profilin RNA and protein levels than the control and these lines were used for further analysis.

EXAMPLE 2

Hypocotyl Regions of Etiolated PFN-U Seedlings Show Severe Phenotype

To investigate whether the shorter phenotype of PFN-U plants and slightly longer phenotype of PFN-O is due to the role of profilin on cell division or cell elongation, the plants were analyzed at the seedling stage. The hypocotyl structure in *Arabidopsis thaliana* is generated entirely during embryogenesis and all the post embryonic growth takes place in the absence of cell division. The elongation of hypocotyl cells is maximum in the etiolated seedlings, which results in elongated hypocotyl structure. This formed the basis for the study on the etiolated hypocotyl. When the seedlings were grown in white light for either 5 days or 10 days, the phenotype was not severe, i.e, the PFN-U seedlings were 20% shorter than control and PFN-O showed no significant difference in size than the control. This could be due to the inhibitory effect of light on hypocotyl elongation. When the seedlings were grown in dark for 5 days or 10 days the PFN-U seedlings showed obvious short phenotype. The phenotype was more pronounced in 10 days seedlings. When compared with the control, 10 days old PFN-U seedlings showed 2x reduction in size of the hypocotyl, whereas PFN-O showed either no difference or slightly taller (10 to 15%) phenotype. The seedlings were germinated in the dark for approximately 25 days at 4° C. and the hypocotyl size was observed in these seedlings. As expected, the wild type growth decreased at this low temperature, while PFN-O seedlings showed an increase in hypocotyl length. The PFN-U seedlings showed a drastic size reduction of three to four times compared to the control. These results suggested that the profilin-1 may be involved in cell elongation especially in the hypocotyl region of Arabidopsis.

Analysis of several parts of transgenic seedlings and mature plants was also carried out to observe phenotypic changes and compared with the wild type seedlings and mature plant. In this analysis, root length, root hair length, petiole length etc. were measured and also the papillae cells, trichomes, pollen tubes, siliques and leaf size were analyzed. Except for trichomes, where there was not much difference between wild type and transgenic plants, all the other data showed that the PFN-U plants showed a reduction in size than the wild type and PFN-O plants either showed no difference or were slightly bigger than the wild type.

EXAMPLE 3

Microscopic Evaluation of Cell Elonaation and Cell Shape

Light Microscopy

To investigate the effect of over- or under-expression of profilin on cell elongation and shape, some light microscopic examination of etiolated hypocotyl regions was performed. Analysis of wild type hypocotyl showed a straight and smooth surface. PFN-O seedlings showed a slightly thicker hypocotyl with straight and smooth surface like wild type, whereas PFN-U seedlings showed the thickest hypocotyl with ruffled surface with dots at several places. In addition to the ruffled surface, some epidermal cells of PFN-U hypocotyl were swollen. A comparison of longitudinal sections of hypocotyl regions of wild type and transgenic seedlings showed the wild type cortex cells to be long and straight, whereas the cortex cells of PFN-O more or less showed no difference from the control. The length of the cortex cells of PFN-U showed approximate 2 fold reduction when compared with the wild type cells. Some of these showed a condensed cell matrix.

Cross sections of mid hypocotyl regions of wild type and transgenic seedlings showed the cell diameter. The wild type hypocotyl showed a single tier of uniform epidermal cells and two layers of cortex cells. In cross section PFN-O showed a thicker hypocotyl. The epidermal and cortex cell arrangement was similar to the wild type but the cells appeared a little bigger, which gave the thicker appearance to the hypocotyl. PFN-U seedlings showed the thickest hypocotyl. Their epidermal cells were not uniform, i.e. some cells were smaller whereas others showed uncontrolled swelling compared to wild type cells. A few epidermal cells appeared in the verge of collapsing and a few other epidermal cells and cortex cells showed condensed cell wall materials.

Electron Microscopy

To confirm the surface ruffling of the PFN-U seedlings, scanning electron microscopic (SEM) analysis of hypocotyl regions of wild type and transgenic seedlings grown in the dark for 10 days at either 22° C. or 25 days at 4° C. was performed. Wild type hypocotyl region in both conditions showed smooth surfaces. The PFN-O showed slightly bigger cells than the control and the smooth surface similar to the wild type control. PFN-U seedlings showed the biggest cells and the hypocotyl surface was highly ruffled. SEM results were highly consistent with the changes observed with the light microscopy.

Electron micrographs of hypocotyl epidermal cell walls of wild type and transgenic seedlings did not show any difference in thickness. While PFN-O seedlings showed no difference from the wild type cells in the cell wall structure, the PFN-U seedlings showed thicker cuticular layer on outer surface. In addition there were regions of the cell where with condensed materials could be observed. The inner sides of these epidermal cells showed some vesicular surfaces which eventually may have been deposited on the cell walls to form the regions with condensed materials. The cortex cell walls of PFN-O seedlings sometimes showed anomalous structures and the PFN-U seedlings showed many vesicles containing electron dense materials near the cell wall.

Role of Profilin-1 in Vesicular Transport

The cell wall plays a key role for the turgor-driven cell growth. The cell wall expansion is a result of the interplay between the synthesis of new components, their regulated incorporation into the existing architecture and the loosening of the structure. Based on this information a defect in cell wall synthesis and maintenance in the hypocotyl of PFN-U seedlings was suspected, as they showed elongation defects. In fact, light and electron microscopy data showed the altered cell walls of epidermal cells and cortex cells of PFN-U hypocotyls. In order to analyze further, the cell structures of these hypocotyls were carefully examined using electron microscopy. There were three different types of condensed materials observed in the endoplasmic reticulum of PFN-U hypocotyl cells—low electron dense fibrils, medium electron dense materials condensing into a ball-like structure, and high electron dense materials. It seemed that these low electron dense particles aggregate to medium dense and finally high electron dense particles, which later accumulate in the wall making the patches. The cortex cells showed similar condensing process of electron dense particles. Numerous ribosomes could be seen attached to the membranes surrounding the fibrous materials and some cortex cells showed ball like structures with condensed fibrous material. In addition to these materials condensed in ER, the cell matrix also showed some vesicles filled with electron dense materials. Some cytochemical detection need to be performed to show whether they are the same or different. Aggregated vesicles were observed in electron micrographs of the epidermal and cortical cells. These aggregated vesicles containing the electron dense materials were eventually transferred to the cell wall. These materials accumulated on the cell wall irregularly, which could be observed on the epidermal and cortex cell walls. Some epidermal cells of PFN-U hypocotyl were smaller than the other cells and are found to contain some fibrous materials. These cells appeared on the verge of collapse.

EXAMPLE 4

Effect of Over- and Under-Expression of Profilin-1 on Flowering Time and Leaf Number The flowering time and leaf number was scored as described above in the materials and methods. The PFN-U plants showed overall smaller phenotype than the PFN-O plants and wild type and flowered at least two weeks earlier than the wild type. The leaf number of PFN-U is at least 40% less than the wild type. On the other hand the PFN-O plants showed a slightly taller phenotype than the wild type plants and there was no significant difference in the flowering time and leaf * number between wild type and PFN-O plants. This suggests that the profilin-1 is involved in the normal flowering time, and when blocked causes a decrease in the flowering time.

EXAMPLE 5

Expression of Profilin-1 in the Elongation Zone of the Roots Tips, Root and the Root Hairs To analyze the expression pattern of the profilin-1 in different tissues/cell types, a profilin-1 promoter-glucuronidase construct was made and homozygous T3 seedlings were generated as described above in materials and methods. A ring of cells in the elongation zone of the root tips and the root hairs of the transgenic plants showed GUS activity.

EXAMPLE 6

Actin Staining Pattern of Wild Type, PFN-O and PFN-U Etiolated Seedlings

It has been shown that overexpression or underexpression of profilins alter the actin cytoskeletal arrangement in *S. pombe, D. discoideum* and CHO cell lines (Balasubramanian et al., 1994; Haugwitz et al., 1994; Finkel et al., 1994). Also the microinjection of profilin into *Tradescantia stamen* hair cells depolymerized the microfilaments and affected cytoplasmic streaming (Staiger et al., 1994). Based on these results the actin cytoskeleton patter of PFN-O and PFN-U seedlings was analyzed and compared with wild type.

Arabidopsis Wild Type Actin Staining Pattern

The actin staining protocol for the etiolated Arabidopsis seedlings was standardized. An abrasive (a lapping compound) was used to enhance greatly the phalloidin penetration into the tissues, particularly the cotyledons. Generally actin arrangement was better preserved in smaller cells i.e. the cells of cotyledons, petioles of cotyledon, and hooks, than larger cells of the hypocotyl which were plasmolyzed and the actin filament organization was severely disrupted. The stomata were not stained, maybe because of the thickened cell walls which were less abraded during tissue preparation and hence less permeable to phalloidin. There was no difference in the actin arrangement between fixed and non-fixed wild type tissue, but the fixation sometimes caused an increased wall fluorescence making it difficult to observe cortical actin filaments. The results are thus based on the comparisons of the non-fixed lines.

All wild type cell types had two subsets of actin cables; thick and thin. The arrangement of these cables varied between tissue types. Cotyledons had random networks of long cables (of varying thickness) which appeared to branch, and many arrays were less dense compared to other tissues making the branching of thicker actin filaments more obvious. Some cells of the petiole and hypocotyl hook had. fine actin filaments in parallel arrays, either transversely or obliquely oriented. In all cells there was another set of thick and wavy actin cables running down the longitudinal axes of the cells. Middle portion cells of the hypocotyl showed long, thick and wavy cables running down the longitudinal axes of the cells. The guard cells in the petiole, showed radial arrays of actin filaments when stained. Young etiolated leaves in 10 days old seedlings had uniformly thickened, co-aligned, either transverse, oblique or longitudinal actin filaments with respect to the leaf axis.

PFN-O and PFN-U Seedlings Show Frequent Normal Actin Staining Pattern

Cotyledons of PFN-O seedlings had actin filaments of varying lengths and thicknesses, randomly oriented in the cortex. The density of the actin filaments fell within the range seen within the wild type cotyledons. One line showed clusters of actin filaments. Petiole hooks and mid hypocotyl regions showed organized arrays as observed in the wild type cells. The cotyledon cells of PFN-U had predominantly abundant cortical actin filaments than wild type but still within the range observed and these were long and randomly oriented. A few cells of one line showed spikes or actin rods as observed with the actin depolymerizing factor overexpression seedlings. The petiole showed similar arrangement of actin filaments as observed in wild type seedlings, but a few seedlings of one line showed spikes. Hook and the mid hypocotyl regions showed actin arrangement similar that of wild type seedlings. Young leaves of both PFN-O and PFN-U showed good actin staining with parallel arrays similar to the wild type.

EXAMPLE 7

Actin and Actin Depolymerizing Factor (ADF) Expression in Profilin Transgenic Plants Over-expression of cofilin/ADF in Dictyostelium, enhanced the actin expression three folds (Aizawa et al., 1996). In order to see whether the profilin over- or under-expression affects the expression patter of actin and ADF in our study, northern and western blots were carried out as described in the materials and methods. The results showed that there was no difference in the expression levels of actin or ADF in the PFN-O or PFN-U plants when compared with the wild type levels of RNA or protein.

Discussion of the Examples

In continuation of the work by Christensen et al. (1996), the in vivo function of profilin-1 of *Arabidopsis thaliana* was analyzed by either over- or under-expressing this protein. Two over-expressing (PFN-O) lines showed a 20 to 30 fold increase in RNA and protein levels, but they did not show any severe phenotype in several growth conditions and the actin architecture was not altered in the cotyledon, petiole and hook cells, when compared with the wild type. Ten-fold profilin overexpression in yeast showed no obvious phenotypic effect, and microinjection of profilin in tissue cultured cells only reduced the centrally located actin filaments, but not the cortical actin filament (Cao et al., 1992). The lack of phenotype could be due to the adaptation of cells to higher profilin levels with possible regulation of the concentrations of other actin monomer binding proteins, other than actin depolymerizing factor, which did not show any change in the amounts in PFN-O or PFN-U plants.

On the other hand, under-expressing (PFN-U) seedlings and mature plants showed dwarf phenotype and were expressing 50% (per seedling basis) to 75% (per microgram basis) of wild type profilin RNA and protein levels. Even though the reduction in protein level is not great, the phenotype was severe. The following points can be considered for an explanation for such moderate reductions in profilin RNA and protein levels.

1. Critical concentration of profilin must be maintained in a cell for its normal function and even slight reduction from this level, as in the case of PFN-U plants, resulted in such a phenotype.

2. Profilin deletions in Dictyostelium (Haugwitz et al., 1994) and in yeast (Haarer et al., 1990) produced severe phenotype, but not lethal, where as in higher eukaryotes like Drosophila profilin deletions resulted in death during late embryonic development (Verheyen and Cooley, 1994) and death of embryo at 100 cell stage of development in mice (Sohn and Goldschmidt-Clermont, 1994). This lethality could be true for plants as well. Complete or partial reduction of profilin concentration below a certain level, in plant cells could be lethal and hence only those cells with moderately reduced profilin levels developed into transgenic plants. This could be another reason for the moderate reduction of profilin protein and RNA levels in PFN-U seedlings.

3. In Dictyostelium deletions of profilin-1 and -2 resulted in a severe phenotype which was rescued by either of the profilins (Haugwitz et al., 1994). Christensen et al., (1996) showed that plant profilins could complement the *Schizosaccharomyces pombe* and *Saccharomyces cerevisiae* profilin mutants. Disruption of the myosin 1B gene caused several subtle effects on the motility which may be accounted for by partial redundancy with other myosins (Wessels et al., 1991.) Profilin-1 is a member of the Arabidopsis profilin gene family, which has been shown to have 3 to 6 members (Christensen et al., 1996) to 8 to 10 members (Huang et al., 1996). The substitutive action (inter and intra species) and/or functional redundancy of profilins could be one of the reasons why lesser levels of profilin RNA and protein in PFN-U seedlings were observed. So deletion or block of a cytoskeletal gene such as profilin appear to have no severe reduction in the levels of protein or RNA as the other genes in the family can compensate the reduction.

In vivo studies on profilin functions has been shown that they are involved in both actin polymerization and depolymerization and microinjection experiments (Staiger et al., 1994), over-expression (Finkel et al., 1994) and under-expression (Haugwitz et al., 1994) experiments showed that the F-actin architecture has generally altered either with an increase or decrease in F-actin content. On the other hand, a Drososphila profilin mutant (chic mutant) showed a defect in oogenesis and nurse cells showed missing actin bundles, whereas the bristles showed increase in number of actin bundles (Verheyen and Cooley, 1994). Also when profilin was microinjected in tissue cultured cells the F-actin filaments are reduced centrally, but unchanged in the cortical region (Cao et al., 1992). In the present work either PFN-O or PFN-U plants, in general, did not show any observable changes in cortical actin architecture of etiolated cotyledon, petiole or hypocotyl hook cells. There could have been subtle changes in the actin arrangement which our method of actin staining failed to pick up.

Profilin has been shown to be involved in cell division and its deletion results in cells with clearly impaired cytokinesis in Dictyostelium (Haugwitz et al., 1994) and *Schizosaccharomyces pombe* (Balasubramanian et al., 1994), abnormal regulation of mitosis in Drosophila (Verheyen and Cooley, 1994), and multinucleation condition in *Saccharomyces cerevisiae* (Haarer et al., 1990). In order to check whether the short phenotype of PFN-U plants are due to such cell division problems entire or sections of etiolated hypocotyl seedlings of PFN-U plants and PFN-O plants were subjected to light and electron microscopy analysis. The results indicated that the cell number in the mid-hypocotyl region did not vary in transgenic seedlings and wild type, and only the cell length of PFN-O cells were reduced which suggested that there is a cell elongation problem rather than a cell division problem. This suggested that profilin-1 may be involved in cell elongation. The profilin-1 promoter-GUS fusion expressed GUS in the root elongation zone and in root hairs and this supports the fact that profilin-1 is needed for the cells that undergo rapid elongation. Vidali et al. (1994) immunolocalized profilin in hypocotyl cells of *Phaseolus vulgaris*. Root hair length measurements of PFN-U seedlings showed that they are shorter than the wild type root hairs. These results provide additional support for the role of profilin in cell elongation. Genetic and physiological studies have also established a role for hormones in the hypocotyl elongation. Auxins and gibberlic acid (GA) act as stimulatory factors for the hypocotyl elongation (Davies, 1995) and GA-deficient or insensitive mutants (Finkelstein and Zeevaart, 1994) as well as auxin resistant mutants (Estelle and Klee, 1994) show dwarf hypocotyls in dark (Lincoln et al., 1990; Desnos et al., 1996). In order to show that the short hypocotyl phenotype of PFN-U plants in fact is not due to the GA or auxin deficiency, the seedlings were grown in appropriate concentrations of GA and Indole acetic acid (IAA). These treatments did not restore the PFN-U seedlings to the wild type size, which suggests that the PFN-U phenotype is not due to hormonal deficiency.

Light and electron microscopic analysis showed shape changes in hypocotyl cells, the epidermal cells in particular, of PFN-U seedlings. The reasons for the cell shape changes in transgenic plants especially PFN-U seedling hypocotyl cells could be due to the following.

1. The elongation defect always associated with a deformation of the hypocotyl surface due to the swelling of epidermal, cortical and endodermal cells. This is true for PFN-U seedlings whose hypocotyl surfaces were ruffled when observed in light and electron microscopes. In cross section these hypocotyls also showed swollen epidermal, cortical and endodermal cells. Such changes were also observed with procuste-1 mutant which showed an elongation defect (Desnos et al., 1996). Actin cytoskeleton has been thought to play a role in cell shape control and defects (Norvick and Bolstein, 1985) or alterations of actin cytoskeleton by cytochalasin treatment (Baskin and Bivens, 1995; Wernicke and Jung, 1992) which caused swelling and irregular shapes of the cell. In addition, enlarged spherical shapes of cells have been reported in cells mutated or under-expressing for actin-associated proteins such as profilin (Haarer et al., 1990) in yeast and in Dictyostelium (Haugwitz et al., 1994). The PFN-U seedlings showed the biggest cell sizes-when compared with wild type and PFN-O seedlings. In these seedlings the cell shape changes could also be due to the changes in the actin cytoskeleton. Some epidermal cells were bigger than the others and some epidermal cells were in the verge of collapsing, reminiscent to the epidermal cell shapes observed for the etiolated hypocotyls of the procuste-1 mutant (Desnos et al., 1996).

2. Plant morphogenesis depends on accurate control over growth anisotropy. Cell shapes other than the spherical shapes are due to the unequal expansion rates in all directions, that is anisotropic expansion. This is due to varying mechanical properties such as turgor pressure in different directions. The cellulose microfibril components of cell walls are deposited in an orderly fashion, and this is generally believed to control the cell shape (Green, 1987). The use of cellulose biosynthesis inhibitor DCB (2,6, dichloro benzonitrile) (Delmer, 1987) caused short and deformed hypocotyl phenotype in the wild type Arabidopsis plants, reminiscent to the prc1 mutant phenotype and PFN-U seedling phenotype. It has been shown that root-expansion mutant rsw is partially defective for the incorporation of radiolabelled glucose into the cellulosic wall fraction (Baskin et al., 1995). Vesicular transport of cell wall materials by exocytqsis is thought to occur with the help of actin cytoskeleton. Dysfunctional actin cytoskeleton impairs such exocytosis which leads to the aberrant cell wall which in turn affects the shape of the cell. Hypocotyls of etiolated PFN-U seedlings showed reduced cell elongation and concomitant stimulation of radial expansion indicating that under-expression of profilin reduced the degree of growth anisotropy. This could be due to a defect in cell wall formation or a block in the transportation of vesicles which carry the cell wall materials. Electron microscopic analysis of etiolated hypocotyl sections of PFN-U plants showed electron dense material release and accumulation on the cell wall of cortex and epidermal cells irregularly. This clearly indicates that there is an obvious defect in the vesicular transport and structure of the cell wall in the profilin under-expressing plants.

Microtubles and microfilaments have been increasingly linked to the general eukaryotic transport apparatus. Actin is implicated in development and maintenance of polarized grown (Norvick and Bolstein, 1985), and in endocytosis in yeast (Reizman, 1993) and mammalian polarized epithelial cells (Gottlieb et al., 1993; Jackman et al., 1994). Fungal actin filaments are thought to be involved in polar transport of vesicles of the exocytosis pathway and consequently in the mechanism of polarized growth (Johnston et al., 1991; Harold, 1991). Fossiner et al. (1996) showed that vesicle dynamics and exocytosis during would wall formation in Characean internodal cells was actin based. Based on these results it was generally assumed that the vesicle based exo- or endocytosis needs the actin cytoskeleton. In hypocotyl of PFN-U seedlings we observed three different kinds of electron dense materials accumulating in the epidermal and cortical cells, including vesicles. This could be due to the fact that profilin under-expression some how alters the actin cytoskeleton, which either by itself or through changes in microtubule cytoskeleton block the vesicular transport in the cells.

Transgenic plants under-expressing profilins flowered at least two weeks earlier than the wild type plants. This suggests a role of profilin at critical concentration and when this level drops the flowering time is reduced. Alternatively, profilin under expression subjects the plants to stress, and as a result the plants flower early. Apart from their role in actin polymerization/depolymerization, profilins have been shown to be involved in tyrosine kinase receptor/phosphoinositide signaling pathway and in Ras/G protein signaling pathway. It also has been shown that profilin binds to poly-L-proline and proline rich sequences. The phenotypes observed in the transgenic plants of the present invention could also be due to block of any or all of the above functions of profilins.

REFERENCES

Aizawa, H., Sutoh, K. And Yahara, I. 1996. Overexpression of cofilin stimulates bundling of actin filaments, membrane ruffling, and cell movement in Dictyostelium. J. Cell. Biol. 132:335–344.

Balasubramanian, M. K., Hirani, B. R., Burke, J. D. and Gould, K. L. 1994. The *Schizosaccaromyces pombe* cdc3+ gene encodes a profilin essential for cytokinesis. Jour. Cell. Biol. 125: 1289–1301.

Baluska, F., Volkmann, D. And Barlow, P. W. 1996. Specialized zones of development in roots: view from the cellular level. Plant Physiol. 112:3–4.

Baskin, T. Herth, W., Cork, A., Birch, R., Rolfe, B., Redmond, J. And Williamson, R. 1995. Radial swelling mutant deficient in cellulose biosynthesis. J. Cell. Bioch. Abstract supplement 21A. 440.

Baskin, T. I. and Bivens, N. J. 1995. Stimulation of radial expansion in Arabidopsis roots by inhibitors of actomyosin and vesicle secretion but not by various inhibitors of metabolism. Planta. 197:514–521.

Beachy, et al. (1985), EMBO J., 4:3047–3053.

Bjorkegren, C., Rozycki, M., Schutt, C. E., Lindberg, U. and Karlsson, R. 1993. Mutagenesis of human profilin locates its poly (L-proline)-binding site to a hydrophobic patch of aromatic amino acids. FEBS Lett. 333: 123–126.

Cao, L. G., Babcock, G. G., Rubenstein P. A. and Wang Y. L. 1992. Effects of profilin and profilactin on actin structure and function in living cells. J. Cell. Biol. 117: 1023–1029.

Christensen, H. E. M., Ramachandran, S., Tan, C. T., Surana, U., Dong, C. H. and Chua, N. H. 1996. Arabidopsis profilins are functionally similar to yeast profilins: Identification of a vascular bundle-specific profilin and a pollen-specific profilin. Plant J. 10: 269–279.

Cooley, L., Verheyen, E. And Ayers, K. 1992. Chickadee encodes a profilin required for intercellular cytoplasm transport during *Drosophila oogenesis*. Cell. 69: 173–184.

Davies, P. J. ed. 1995. Plant hormones. Physiology, biochemistry and molecular biology. Dordrecht. The Netherlands: Kluwer Academic Publishers.

Delmer, D. P. 1987. Cellulose biosynthesis. Ann. Rev. Plant Pysiol. 38: 259–290.

Desnos, T., Orbovic, V., Bellini, C., Kronenberger, J., Caboche, M., Trass, J. And Hofte, H. 1996. Procustel mutants identify two distinct genetic pathways controlling hypocotyl cell elongation, respectively in dark-and light-grown Arabidopsis. Development. 122: 683–693.

Drobak, B. K., Watkins, P. A. C., Valenta, R., Dove, S. K., Lloyd, C. W. and Staiger, C. i. 1994. Inhibition of plant plasma membrane phosphoinositide phospholipase C by the actin-binding protein, profilin. Plant J. 6: 389–400.

Estelle, M. and Klee H. J. 1994. Auxin and cytokinin in Arabidopsis. In Arabidopsis. (Ed E. M. Myerowitz and C. R. Sommerrville). pp. 555–578. Cold Spring Harbour, N.Y. Cold Spring Harbour Laboratory press.

Finkel, T., Theriot, J. A., Dise, K. R., Tomaselli, G. F. and Goldschmidt-Clermont, P. J. 1984. Dynamic actin structures stabilized by profilins. Proc. Natl. Acad. Sci. 91: 1510–1514.

Finkelstein, R. R. and Zeevaart, I. A. D. 1994. Gibberlin and abscisic acid biosynthesis and response. In Arabidopsis. (Ed. E. M. Meyerowitz and C. R. Sommerrville). pp. 523–553. Cold Spring Harbour, N.Y. Cold Spring Harbour Laboratory press.

Fossner, I., Lichtscheidl, I. K. and Wasteneys, G. O. 1996. Actin-based vesicle dynamics and exocytosis during wound wall formation in characean internodal cells. Cell Motil. Cytoskel. 35: 35–48.

Giehl, K., Valenta, R., Rothkegel, M., Ronsiek, M., Mannherz, H. G. and Jockusch, B. M. 1994. Interaction of plant profilin with mammalian actin. Eur. J. Biochem. 226: 681–689.

Goldschmidt-Clermont, P. J., Kim, J. W., Machesky, L. M., Rhee, S. G. and Pollard, T. D. 1991. Regulation of phospholipase C-1 by profilin and tyrosine phosphorylation. Science, 251: 1231–1233.

Goldschmidt-Clermont, P. J., Machesky, L. M. Baldassare, J. J. and Pollard, T. D. 1990. The actin-binding protein profilin binds to PIP2 and inhibits its hydrolysis by phospholipase C. Science 247: 1575–1578.

Gottlieb, T. A., Ivanov, I. E., Adesnik, M. And Sabatini, D. D. 1993. J. Cell Biol. 120: 695–710.

Green, P. B. 1987. Inheritance of pattern: analysis from phenotype to gene. Am Zool. 27: 657–673.

Haarer, B. K., Lillie, S. H., Adams, A. E. M., Magdolen, V., Bandlow, W. And Brown, S. S. 1990. Purification of profilin from Saccharomyces cerevisiae and analysis of profilin-deficient cells. J. Cell Biol. 110: 105–114.

Haffner, C. Jarchau, T., Reinhard, M., Hoppe, J., Lohmann, S. M. and Walter, U. 1995. Molecular cloning, structural analysis and functional expression of the proline-rich focal adhesion and microfilament-associated protein VASP. EMBO J. 14: 19–27.

Harold, F. M. 1991. Biochemical topology: from vectorial metabolism to morphogenesis. Biosci. Rep. 11: 347–385.

Haugwitz, M., Noegel, A. A., Karakesisoglou, J. And Schleider, M. 1994. Dictyostelium amoebae that lack G-actin-sequestering profilins show defects in F-actin content, cytokinesis, and development. Cell 79: 303–314.

Huang, S., McDowell, J. M., Weise, M. J. and Meagher, R. B. 1996. The Arabidopsis profilin gene family. Plant physiol. 111: 115–126.

Jackman, M. R., Shurety, W., Ellis, J. A. and Luzio, J. P. 1994. J. Cell Sci. 107: 2547–2556.

Jefferson, R. A. 1987. Assaying chimeric genes in plants: The GUS gene fusion system. Plant Mol. Biol. Rep. 5: 387–405.

Johnston, G. C., Prendergast, J. A. and Singer, B. A. 1991. The Saccharomyces cerevisiae MYO2 gene encoding an essential myosin for vectorial transport of vesicles. J. Cell Biol. 113: 539–551.

Laemmli, U. K. 1970. Cleavage of structural proteins during the assembly of the head of bacteriophage T4. Nature. 227: 680–685.

Lincoln, C., Britton, J. H. and Estelle, M. 1990. Growth and development of the axrl mutants of Arabidopsis. The Plant Cell. 2: 1071–1080.

Meagher, R. B. and Williamson, R. E. 1994. The plant cytoskeleton. Cold Spring Harbour Laboratory Press. Pp 1049–1084.

Mittermann, I., Swoboda, I., Pierson, E., Eller, N., Kraft, D., Valenta, R. And Heberle-Bors, E. 1995. Molecular cloning and characterization of profilin from tobacco (*Nicotiana tobacum*): increased profilin expression during pollen maturation. Plant Mol. Biol. 27: 137–146.

Norvick, P. and Bolstein D. 1985. Cell. 40: 405–416.

Perelroizen, I., Didry, D., Christensen H., Chua, N. H. and Carlier, M. F. 1996. Role of nucleotide exchange and hydrolysis in the function of profilin in actin assembly. J. Biol. Chem. 271: 12302.

Reinhard, M., Giehl, K., Abel, K., Haffner, C., Jarchau, T. Hoppe, V., Jockusch, B. M. and Walter, U. 1995. The proline-rich focal adhesion and microfilament protein VASP is a ligand for profilins. EMBO J. 14: 1583–1589.

Reizman, H. 1993. Trends Cell Biol. 3: 273–277.

Riggs, et al. (1989) Plant Science, 63:47–57.

Ruhlandt, G., Lange, U. and Grolig, F. 1995. Profilins purified from higher plants bind to actin from cardiac muscle and to actin from green algae. EMBO J. 14: 1583–1589.

Salinas, J., Ooda, K. and Chua N. H. (1992) Two G-Box-related sequences confer different expression paterns in transgenic tobacco. Plant Cell. Vol. 4:1485–1493.

Sohn, R. H., Chen, J., Koblan, K. S., Bray, P. Fl and Goldschmidt-Clermont, P. J. 1995. Location of a binding site for phospatidylinositol 4,5-bisphosphate on human profilin. J. Biol. Chem. 270: 21114–21120.

Sohn, R. H. and Goldschmidt-Clermont, P. J. 1994. Profilin: At the crossroads of signal transduction and the actin cytoskeleton. BioEssays 16: 465–472.

Staiger, C. J., Goodbody, K. C., Hussey, P. J., Valenta R., Drobak, B. J. and Lloyd, C. W. 1993. The profilin multigene family of maize: differential expression of three isoforms. Plant J. 4: 631–641.

Staiger, C. J., Yuan, M., Valenta, R., Shaw, P. J., and, R. M. and Lloyd, C. W. 1994. Microinjected profilin affects cytoplasmic streaming in plant cells by rapidly depolymerizing actin microfilaments. Curr. Biol. 4: 215–219.

Sun, H., Kwiatkowska, K. and Yin, H. L. 1995. Actin monomer binding proteins. Curr. Biol. 7: 102–110.

Theriot, J. A. and Mitchison, T. J. 1993. The three faces of profilin. Cell. 75: 835–838.

Toriyama, K., Thorsness, M. K. Nasarallah, M. E. and Nasarallah, J. B. 1991. A Brassica S locus gene promoter directs sporophytic expression in the anther tapetum of transgenic Arabidopsis. Devel. Biol. 143: 427–431.

Valenta, R., Ferreira, F., Grote M., Swoboda, I., Vrtala, S., Duchene, M., Deviller, P., Meagher, R. M., McKinney, E., Heberle-Bors, E., Kraft, D. And Scheiner, O. 1993. Identification of profilin as an actin-binding protein in higher plants. J. Biol. Chem. 268: 22777–22781.

Verheyen, E. M. and Cooley, L. 1994. Profilin mutations disrupts multiple actin-dependent processes during Drosophila development. Develop. 120: 717–728.

Vidali, L., Perez, H. E., Lopez, V. V., Noguez R., Zamudio, F. And Sanchez, F. 1995. Purification, characterization, and cDNA cloning of profilin from *phaseolus Vulgaris*. Plant Physiol. 108: 115–123.

Vojtek, A., Haarer, B., Field, J., Gerst, J., Pollard, T. D., Brown, S. And Wigler, M. 1991. Evidence for a functional link between profilin and CAP in the yeast *S. cerevisiae*. Cell, 66: 497–505.

Wernicke, W. And Jung, G. 1992. Role of cytoskeleton in cell shaping of developing mesophyll of wheat (*Triticum aestivum L.*) Dur. J. Cell Biol. 57: 88–94.

Wessels, D., Murray, J., Jung, G., Hammer, J. A. and Soll, D. R. 1991. Myosin 1B null mutants of Dictyostelium exhibit abnormalities in motility. Cell Motil. Cytoskel. 20: 301–315.

Williamson, R. E. 1993. Organelle movements. Annu. Rev. Plant Physiol. Plant Mol. Biol. 44: 181–202.

We claim:

1. A method for increasing the size of a plant or its parts comprising a) transforming a plant or plant cell with a gene capable of expressing a profilin in the plant, b) growing the plant or regenerating a whole plant from the transformed plant cell and c) causing the transformed gene to be expressed in the plant such that an increase in size of the plant or its parts results, when compared to a non-transgenic plant, and its parts, of the same type.

2. The method of claim 1 wherein the profilin is selected from the group consisting of profilin-1, profilin-2, profilin-3 and profilin-4.

3. The method of claim 2 wherein the profilin is profilin-1.

4. The method of claim 1 wherein the plant or plant cell is a dicot plant or plant cell.

5. The method of claim 1 which results in a plant with a tall phenotype.

6. The method of claim 1 which results in a plant With an expanded root and root hair system.

7. The method of claim 6 wherein the profilin is selected from the group consisting of profilin-1, profiln-2, profilin-3 and profilin-4.

8. The method of claim 7 wherein the profilin is profilin-1.

9. The method of claim 5 wherein the plant or plant cell is a dicot plant or plant cell.

\* \* \* \* \*